United States Patent [19]

Potts

[11] 4,186,153

[45] Jan. 29, 1980

[54] PROCESS FOR 1,2,4,5-TETRACHLOROBENZENE

[75] Inventor: Irwin W. Potts, Midland, Mich.

[73] Assignee: The Dow Chemical Company, Midland, Mich.

[21] Appl. No.: 869,562

[22] Filed: Jan. 16, 1978

[51] Int. Cl.$^2$ .............................................. C07C 25/00
[52] U.S. Cl. ................................................ 260/650 R
[58] Field of Search ................................... 260/650 R

[56] References Cited
U.S. PATENT DOCUMENTS 3,557,227  1/1971  Fooladi ............................. 260/65 D

OTHER PUBLICATIONS

Keefer & Andrews, JACS 79, pp. 4348–4353, (1957).

Primary Examiner—Delbert E. Gantz
Assistant Examiner—Joseph A. Boska
Attorney, Agent, or Firm—G. R. Plotecher

[57] ABSTRACT

The process for preparing 1,2,4,5-tetrachlorobenzene, the process comprising contacting at reactive conditions 1,2,4-trichlorobenzene and chlorine gas in the presence of a catalytic amount of at least one Lewis acid, such as ferric trichloride, is improved by using as a cocatalyst at least one iodoaryl compound, such as p-iodoanisole.

9 Claims, No Drawings

PROCESS FOR 1,2,4,5-TETRACHLOROBENZENE

BACKGROUND OF THE INVENTION

1. Field of the Invention

This invention relates to an improved process for preparing 1,2,4,5-tetrachlorobenzene.

2. Description of the Prior Art

The production of 1,2,4,5-tetrachlorobenzene from a Lewis acid-catalyzed contacting of 1,2,4-trichlorobenzene and chlorine gas is known. However, for each pound of desired isomer produced, about 0.5 pounds of undesired isomers and tars are also produced. This latter material has little or no utility whereas the former material is a precursor of 2,4,5-trichloro-phenol, an intermediate to many valuable, biologically active compounds. Any improvement in the yield of the 1,2,4,5-isomer is therefore desirable.

SUMMARY OF THE INVENTION

According to this invention, the process for preparing 1,2,4,5-tetrachlorobenzene, the process comprising contacting at reactive conditions 1,2,4-trichlorobenzene and chlorine gas in the presence of a catalytic amount of at least one Lewis acid is improved by using as a cocatalyst at least one iodoaryl compound of the formula:

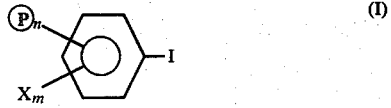

wherein X is a substituent which has less affinity for electrons than does hydrogen, Ⓟ is a polymer backbone, m is an integer of 0–3, and n is 0 or 1. This cocatalyst system demonstrates enhanced regioselectivity for 1,2,4,5-tetrachlorobenzene (as compared to systems of Lewis acids alone), thus reducing the formation of other tetra isomers and tar.

DETAILED DESCRIPTION OF THE INVENTION

The iodoaryl compounds (I) of this invention include both polymeric (n is 1) and nonpolymeric (n is 0) compounds. Typically, the nonpolymeric compounds have on the benzene nucleus at least one substituent (m is at least 1) which has less affinity for electrons than does hydrogen. These substituents can be ortho, meta and/or para to the iodo moiety but those compounds having at least one substituent in the para position are preferred. Preferred substituents can be further defined as having a Hammett sigma value of less than about negative 0.1 (wherein the sigma value is determined by using a benzoic acid ionization standard as described by E. S. Gould, *Mechanism and Structure in Organic Chemistry*, p. 221, Holt, Reinhart & Winston (N.Y., 1959)). Typical substituents include alkyl, such as methyl, ethyl, propyl, isopropyl, pentyl, neopentyl, decyl, etc.; alkoxy, such as methoxy, ethoxy, propoxy, butoxy, etc.; halogen, such as chlorine, bromine, iodine, etc.; amino, such as amine (—NH₂), methylamine, dimethylamine, ethylamine, diethylamine, etc.; aryl, such as phenyl, tolyl, xylyl, etc. and the like. $C_1$–$C_6$ alkyl and $C_1$–$C_6$ alkoxy are the preferred substituents and $C_1$–$C_6$ alkoxy are the most preferred substituents.

Representative nonpolymeric iodoaryl compounds include: iodobenzene; alkyl iodobenzenes, such as o-, m- and p-iodotoluene, 1-iodo-4-ethylbenzene, 1-iodo-3,4-diethylbenzene, 1-iodo-4-propylbenzene, 1-iodo-4-dodecylbenzene, etc.; alkoxyiodobenzenes, such as p-iodoanisole, 1-iodo-3-methoxy-4-ethoxybenzene, 1-iodo-4-ethoxybenzene, 1-iodo-4-butoxybenzene, 1-iodo-4-hexoxybenzene, etc.; halide iodobenzenes, such as 1,4-diiodobenzene, 1-iodo-4-chlorobenzene, 1-iodo-3,4-dichlorobenzene, 1-iodo-4-fluorobenzene, etc.; amino iodobenzene, such as o-, m- and p-iodoaniline, p-iodoacetanilyde, 1-iodo-4-methylamine benzene, 1-iodo-4-diethylamine benzene, etc.; and aryliodobenzenes, such as p-phenyliodobenzene, p-phenethyliodobenzene, etc.

Although the benzene nuclei of the polymeric iodoaryl compounds can bear the same kind (X) and number (m) of substituents as the nonpolymeric compounds, typically the benzene nuclei of the polymeric compounds do not bear any substituents (m is 0) other than the polymer backbone or matrix Ⓟ itself. The backbone, like the substituents on the nonpolymeric compounds, can also be ortho, meta or para to the iodo moiety but it too is preferably in the para position. Moreover, the composition of the backbone is not critical to the practice of this invention and can thus be varied to convenience. Representative polymeric iodoaryl compounds include those prepared from the iodination of such materials as cross-linked polystyrene beads, diphenyloxide-formaldehyde resins, etc.

The iodoaryl compounds are used in combination with at least one Lewis acid catalyst. Any Lewis acid that can catalyze the chlorination of 1,2,4-trichlorobenzene can be here used. Illustrative Lewis acids include: manganese dichloride, zinc dichloride, titanium tetrachloride, tin tetrachloride, antimony trichloride, aluminum trichloride, ferric trichloride, etc. Lewis acids containing other halogen atoms, such as aluminum tribromide, ferric dibromochloride, etc. can also be here used but are generally disfavored because of possible halogen exchange with the starting materials (chlorinated benzenes) and resulting contamination of the end product. Because of their superior catalytic activity, ferric, antimony and aluminum trichloride are preferred Lewis acids with ferric trichloride generally most preferred. The Lewis acids of this invention can be used per se or generated in situ.

Any combination of iodoaryl compound and Lewis acid that will demonstrate an enhanced regioselectivity for 1,2,4,5-tetrachlorobenzene can form the cocatalyst system of this invention. Typically, the cocatalyst system comprises one Lewis acid and one iodoaryl compound but cocatalyst systems comprising more than one Lewis acid and/or more than one iodoaryl compound can also be used. The respective amounts of Lewis acid(s) and iodoaryl compound(s) in the cocatalyst system will vary with individual combinations but combinations having a minimum iodoaryl compound:Lewis acid mole ratio (or mole equivalents ratio if the iodoaryl compound is a polymeric compound) of about 0.5:1 are preferred, with a minimum mole ratio of about 1:1 most preferred. The preferred maximum iodoaryl compound:Lewis acid mole ratio is about 4:1, with a maximum mole ratio of 2:1 most preferred. The iodoaryl compound must be used in combination with the Lewis acid because unlike the Lewis acid, the iodoaryl compound alone will not catalyze the chlorination of 1,2,4-trichlorobenzene.

A catalytic amount of the cocatalyst system is used in the chlorination of 1,2,4-trichlorobenzene to 1,2,4,5-tetrachlorobenzene. Typically, a minimum amount of about 0.2 mole percent (based upon the 1,2,4-trichlorobenzene) of cocatalyst system is used and preferably about 0.4 mole percent. Practical considerations, such as convenience, economy, etc., are the only limitations upon the maximum amount of cocatalyst system that can be employed, but generally a maximum of about 1 mole percent, and preferably about 0.8 mole percent, is used.

The cocatalyst system of this invention is used in the same manner as the Lewis acid catalyst is used in the known process for preparing 1,2,4,5-tetrachlorobenzene from 1,2,4-trichlorobenzene. Typically, in the presence of a cocatalyst system, chlorine gas is bubbled into the starting material which contains 1,2,4-trichlorobenzene but generally also contains benzene, chlorobenzene, dichlorobenzenes and other trichlorobenzene isomers. Some of these other starting materials are eventually converted to 1,2,4-trichlorobenzene during the course of the process. The starting material is maintained at reactive conditions which can vary with the cocatalyst system employed. Where cocatalyst systems comprising antimony, aluminum or ferric trichloride are used, conditions generally between about 40° C. and 120° C., and preferably between about 60° C. and about 90° C., are employed. Atmospheric pressure is typically employed although superatmospheric pressure can also be used if desired. Further description of the conventional chlorination process is given by Fooladi, U.S. Pat. No. 3,557,227.

The following examples are illustrative embodiments of this invention. Unless indicated to the contrary, all parts and percentages are by weight.

SPECIFIC EMBODIMENTS

Procedure

The following examples were performed in a one-liter, 3-neck, round-bottom flask equipped with a thermometer, gas sparger tube, air-powered stirrer and a reflux condenser connected to a dry ice-acetone trap. The trap was connected to a hydrogen chloride scrubber by rubber tubing. Temperature was controlled by use of an infrared lamp and a cooling gun both of which were connected to and controlled by a Matheson Lab Stat. A mixture of 1,2,4-trichlorobenzene (500 g, purity>99 percent) and a cocatalyst system consisting of ferric trichloride (0.15 percent) and an iodoaryl compound (equivalent of 0.15 percent iodine) were used in each experiment. Chlorine gas was metered into the mixture through a calibrated rotometer at 48 g/hr. The iodoaryls here used were commercial grade and were not further purified except for 1,2-dichloro-4-iodobenzene which was first washed with ethanol and then vacuum dried before use. Samples of the reaction mixture were periodically removed, washed with a saturated sodium carbonate solution, dried over sodium sulfate and subsequently analyzed by gas chromatography (GC).

EXAMPLES 1–18

Various iodoaryl compounds were employed as cocatalysts according to the above-described procedure. After reaching the freezing point of the solution at the various temperatures, a sample was withdrawn and subjected to GC analysis. The results are reported in Table I.

As a basis of comparison, the use in the above-described procedure of ferric trichloride alone generates a 1,2,4,5-/1,2,3,4-tetrachlorobenzene mole ratio of about 2.

TABLE I
CHLORINATION OF 1,2,4-TRICHLOROBENZENE WITH A FERRIC CHLORIDE-NONPOLYMERIC IODOARYL COMPOUND COCATALYST SYSTEM[1]

| Ex. | Iodoaryl[2] | Temp. (°C.) | Mole % Composition at Freezing Point[3] | | | Ratio[4] |
|---|---|---|---|---|---|---|
| | | | 1,2,4 | 1,2,4,5 | 1,2,3,4 | |
| 1 | A | 40 | 84.81 | 11.67 | 3.29 | 3.55 |
| 2 | A | 40 | 81.74 | 13.50 | 4.09 | 3.30 |
| 3 | A | 40 | 84.01 | 12.56 | 3.39 | 3.71 |
| 4 | A | 40 | 84.25 | 12.39 | 3.35 | 3.70 |
| 5 | A | 80 | 70.55 | 22.91 | 6.53 | 3.51 |
| 6 | A | 80 | 59.39 | 31.52 | 9.08 | 3.47 |
| 7 | B | 40 | 82.81 | 13.67 | 3.43 | 3.94 |
| 8 | B | 40 | 82.79 | 13.78 | 3.44 | 4.01 |
| 9 | B | 80 | 64.63 | 27.58 | 7.76 | 3.55 |
| 10 | B | 80 | 69.12 | 24.13 | 6.74 | 3.58 |
| 11 | C | 40 | 87.60 | 10.16 | 2.19 | 4.64 |
| 12 | C | 40 | 86.10 | 11.61 | 2.25 | 5.16 |
| 13 | D | 40 | 86.09 | 11.01 | 2.84 | 3.88 |
| 14 | D | 40 | 85.17 | 11.85 | 2.93 | 4.04 |
| 15 | E | 40 | 84.48 | 11.54 | 3.93 | 2.94 |
| 16 | F | 40 | 84.64 | 11.61 | 3.25 | 3.57 |
| 17 | F | 40 | 84.09 | 12.53 | 3.35 | 3.74 |
| 18 | G | 40 | 83.24 | 13.44 | 3.26 | 4.12 |

Footnotes:
[1] Examples 1–18 produced no detectable amount of pentachlorobenzene.
[2] A = 1,2-dichloro-4-iodobenzene
B = 1-iodo-4-chlorobenzene
C = p-iodoanisole
D = p-iodotoluene
E = 1-iodo-4-nitrobenzene
F = m-diiodobenzene
G = iodobenzene
[3] Freezing point of the mixture at the specified temperature.
[4] 1,2,4,5-/1,2,3,4-tetrachlorobenzene mole ratio.

Control

An experiment was performed according to the above-described procedure except that the catalyst consisted only of 1-iodo-4-chlorobenzene, i.e., no ferric chloride was present. The reaction was conducted at 40° C. and atmospheric pressure. After several minutes of contact, no detectable amounts of either 1,2,4,5- or 1,2,3,4-tetrachlorobenzene were observed. This data demonstrates that an iodoaryl compound by itself will not catalyze the chlorination of 1,2,4-trichlorobenzene.

EXAMPLES 19 and 20

The procedure of Examples 1–18 was twice repeated except that antimony trichloride was substituted for ferric trichloride in the first repetition and that aluminum trichloride was substituted for ferric trichloride in the second repetition (both repetitions using 1-iodo-4-chlorobenzene as the iodoaryl compound and a 60° C. contacting temperature). The 1,2,4,5-:1,2,3,4-tetrachlorobenzene mole ratio for the first repetition was about 2.8 and for the second repetition was about 2.75.

EXAMPLES 21–24

Polymer Preparation

Polystyrene beads (56 g) cross-linked with 8 percent divinylbenzene, iodine (63.45 g) and perchloroethylene (200 ml) were charged to a three-neck flask equipped with a dropping funnel, stirrer, thermometer and condenser. The dropping funnel was filled with nitric acid (100 ml, 70 percent) and the flask heated to about 100° C. with an infrared heating lamp. The nitric acid was added dropwise over a period of 4 hours and then the resulting mixture was post-reacted for an additional hour. Nitrogen was bubbled through the mixture to remove residual hydrogen iodide and nitrogen oxides. The iodinated resin was removed by filtration and sequentially washed with 400 ml of 8 percent sodium hydroxide, 500 ml of water and 1000 ml of perchloroethylene. The resin was then dried overnight in a vacuum oven at 30 inches Hg and 60° C. Analyses of this resin showed that it contained 45.5±0.9% iodine, 6±1% chlorine and 0.73-0.87% nitrogen. This resin is designated "Catalyst A" in Table II.

A diphenyl oxide-formaldehyde polymer was iodinated in a manner analogous to the polystyrene beads. Polymer (79.4 g) and iodine (55 g) were added to perchloroethylene (200 ml) with the subsequent addition over 6 hours of nitric acid (100 ml, 70 percent). The resulting iodinated polymer was then removed by filtration, washed and dried overnight. Analysis: 27.5±0.5% iodine; 1.08% nitrogen. This resin is designated "Catalyst B" in Table II.

Chlorination of 1,2,4-Trichlorobenzene

Catalytic resin (2 g) and anhydrous ferric trichloride (0.375 g) were added to 1,2,4-trichlorobenzene (250 g). The resulting reaction mixture was then heated to the desired temperature and subsequently sparged with chlorine. Samples were periodically removed, washed with saturated sodium carbonate solution, dried over anhydrous sodium sulfate and analyzed by GC. The results are reported in Table II.

The preceding examples were for illustrative purposes only and are not to be construed as limitations upon the invention. The skilled artisan will recognize that many variations can be made on this invention without departing from the spirit and scope of the appended claims.

TABLE II

CHLORINATION OF 1,2,4-TRICHLOROBENZENE WITH A FERRIC CHLORIDE-POLYMERIC IODOARYL COMPOUND COCATALYST SYSTEM

| Ex. | Catalyst | Temp. (°C.) | Mole % Composition at Freezing Point[1] | | | | Ratio[3] |
|---|---|---|---|---|---|---|---|
| | | | 1,2,4 | 1,2,4,5 | 1,2,3,4 | Penta[2] | |
| 21 | A | 40 | 82.51 | 12.58 | 4.65 | — | 2.7 |
| 22 | A | 40 | 67.16 | 23.27 | 9.18 | 0.34 | 2.5 |
| 23 | B | 45 | 80.00 | 13.89 | 5.73 | 0.14 | 2.4 |
| 24 | B | 80 | 65.84 | 22.60 | 11.17 | 0.52 | 2.0 |

[1]Freezing point of the mixture at the specified temperature.
[2]Pentachlorobenzene.
[3]1,2,4,5-/(1,2,3,4-tetrachlorobenzene + penta) mole ratio.

What is claimed is:

1. In the process of preparing 1,2,4,5-tetrachlorobenzene, the process comprising contacting at reactive conditions 1,2,4-trichlorobenzene and chlorine gas in the presence of a catalytic amount of Lewis acid, the improvement comprising using as a cocatalyst at least one iodoaryl compound of the formula

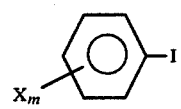

wherein X is a substituent which has less affinity for electrons than does hydrogen, and m is an integer of 0-3.

2. The process of claim 1 wherein m is at least 1.

3. The process of claim 2 wherein at least one X is para to the iodo moiety.

4. The process of claim 3 wherein X is $C_1$-$C_6$ alkyl or $C_1$-$C_6$ alkoxy.

5. The process of claim 4 wherein the Lewis acid is antimony, aluminum or ferric trichloride.

6. The process of claim 5 wherein the iodoaryl compound and Lewis acid are present at an iodoaryl compound:Lewis acid mole ratio of about 0.5:1 to about 4:1.

7. The process of claim 6 wherein the cocatalyst system of Lewis acid and iodoaryl compound is present in an amount of about 0.2 to about 1 mole percent based upon the 1,2,4-trichlorobenzene.

8. The process of claim 7 wherein the Lewis acid is ferric trichloride.

9. The process of claim 8 wherein the reaction conditions are a temperature between about 40° C. and about 120° C. and about atmospheric pressure.

* * * * *